US010449092B2

(12) United States Patent
Shuman

(10) Patent No.: US 10,449,092 B2
(45) Date of Patent: Oct. 22, 2019

(54) UTILITY DEVICE FOR REMOVING EARWAX

(71) Applicant: UTILITYTIP.COM LLC, Idaho Falls, ID (US)

(72) Inventor: Jake Ryan Shuman, Ammon, ID (US)

(73) Assignee: UTILITYTIP.COM LLC, Idaho Falls, ID (US)

( * ) Notice: Subject to any disclaimer, the term of this patent is extended or adjusted under 35 U.S.C. 154(b) by 266 days.

(21) Appl. No.: 15/428,935

(22) Filed: Feb. 9, 2017

(65) Prior Publication Data

US 2017/0224537 A1 Aug. 10, 2017

Related U.S. Application Data

(60) Provisional application No. 62/293,266, filed on Feb. 9, 2016, provisional application No. 62/411,477, filed on Oct. 21, 2016.

(51) Int. Cl.
*A61F 11/00* (2006.01)

(52) U.S. Cl.
CPC .................................. *A61F 11/006* (2013.01)

(58) Field of Classification Search
CPC ............................... A61F 11/006; B08B 1/003
USPC .................................................. 606/161, 162
See application file for complete search history.

(56) References Cited

U.S. PATENT DOCUMENTS 2,583,750 A 1/1952 Runnels
4,568,326 A 2/1986 Rangaswamy
4,746,238 A 5/1988 Levine
5,374,276 A 12/1994 Lay
5,632,756 A 5/1997 Kruglick
5,715,559 A 2/1998 Mitri
6,033,417 A 3/2000 Tseng
D432,239 S 10/2000 Shimizu
7,658,745 B2 2/2010 Olson
8,777,972 B2 7/2014 Burres
9,233,027 B1 1/2016 Jackson
(Continued)

FOREIGN PATENT DOCUMENTS

CN 1224340 7/1999
CN 100397974 7/2008
(Continued)

OTHER PUBLICATIONS

Aliex Press, "Stainless Steel Dual Ended Spiral Earpick Ear Wax Remover . . . ", downloaded Feb. 16, 2016 from www.aliexpress.com/item/Stainless-Steel-Dual-Ended-Spiral-Earpick-Ear-Scratch-Stick-Ear-Digging-Cleaning-Tool/32348462776; 4 pages.
(Continued)

*Primary Examiner* — Tuan V Nguyen
(74) *Attorney, Agent, or Firm* — Knobbe, Martens, Olson & Bear, LLP

(57) ABSTRACT

A utility device is provided for insertion into an ear. The utility device comprises a first tip portion. The first tip portion can include a first end, a base, a plurality of first ridges extending between the first end and the base, and a plurality of second ridges extending between each of the plurality of first ridges. The utility device can include an intermediate region and a central portion. The intermediate portion can connect the central portion to the first tip portion. The central portion can allow a user to grip and/or hold the utility device.

17 Claims, 9 Drawing Sheets

100
118
122
124
114
114
108
128B
102
128A
120
130
110
112
110
128
104
106

(56) References Cited

U.S. PATENT DOCUMENTS

| | | | | |
|---|---|---|---|---|
| 2005/0096678 | A1 | 5/2005 | Olson | |
| 2008/0300527 | A1 | 12/2008 | Bivins | |
| 2009/0173650 | A1 | 7/2009 | Stein et al. | |
| 2011/0264060 | A1 | 10/2011 | Siniawski et al. | |
| 2012/0296355 | A1* | 11/2012 | Burres .................. | A61F 11/006 606/162 |
| 2013/0116596 | A1 | 5/2013 | Birnboim et al. | |
| 2015/0018861 | A1 | 1/2015 | Olson | |

FOREIGN PATENT DOCUMENTS

| | | |
|---|---|---|
| CN | 204363873 | 6/2015 |
| CN | 105193531 | 12/2015 |
| DE | 102004057109 | 6/2006 |
| DE | 102012005483 | 9/2013 |
| DE | 202013103307 | 10/2014 |
| JP | 2008220492 | 9/2008 |
| JP | 2011036605 | 2/2011 |
| JP | 2011115346 | 6/2011 |
| WO | WO 2010133736 | 11/2010 |
| WO | WO 2015083161 | 6/2015 |

OTHER PUBLICATIONS

Clinere, "Clinere Products: Scoop", downloaded Feb. 16, 2016 from www.clinere.com/products/html; 3 pages Aliex Press, "Product of Hepster—Ear Wax Ear Pick Cleaner Curette Screw Remover . . . ", downloaded Feb. 16, 2016 from www.aliexpress.com/item/Ear-Wax-Ear-Pick-Cleaner-Curette-Screw-Remover-Stick-Stainless-Steel-Pick-Tool-PTSP/1995887976.html?spm=2114.4, 10 pages.

* cited by examiner

UTILITY DEVICE FOR REMOVING EARWAX

INCORPORATION BY REFERENCE TO ANY PRIORITY APPLICATIONS

This application claims the priority benefit under 35 U.S.C. § 119(e) of U.S. Provisional Application No. 62/411,477, filed Oct. 21, 2016, and U.S. Provisional Application No. 62/293,266, filed Feb. 9, 2016, the entire contents of which are hereby incorporated by reference and should be considered a part of this specification. Any and all applications for which a foreign or domestic priority claim is identified in the Application Data Sheet as filed with the present application are hereby incorporated by reference under 37 C.F.R. § 1.57.

FIELD OF THE DISCLOSURE

The present disclosure relates to the field of utility devices for personal care. In particular, the present disclosure relates to utility devices for removing earwax.

BACKGROUND

In certain situations, undesirable material build-up, such as earwax, dust, dirt, and/or or fluids, among others can become adhered, and/or lodged in difficult-to-reach areas. In such circumstances, it may be difficult to clean the targeted areas or surfaces. Similarly, it may be difficult to remove the undesirable material build-up from the targeted areas or surfaces without damaging or harming the area or surface. For example, it can be difficult to effectively clean the inside of a user's ear without damaging the user's skin. Additionally, it can be difficult to reach and/or clean the inside of a user's ear without re-inserting a device multiple times.

SUMMARY OF THE DISCLOSURE

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

According to some embodiments, a utility device is configured for insertion into an ear. The utility device can comprise: a first central core; a first tip portion surrounding the first central core; an intermediate region; and a central portion configured to allow a user to hold the utility device. The first tip portion can include a first end; a base; a plurality of first ridges extending radially outward from the first central core and extending from the first end of the first tip portion to the base of the first tip portion; and a plurality of second ridges. The plurality of first ridges includes a first sidewall and a second sidewall connected by an outer surface. The plurality of second ridges include a top wall and a bottom wall, wherein the plurality of second ridges include a top wall and a bottom wall, wherein the top wall and the bottom wall form a second ridge edge at the intersection between the top wall and the bottom wall, wherein the second ridge edge extends between the first side wall and the second side wall of adjacent first ridges of the plurality of first ridges such that the plurality of second ridges extend radially outward from the central core to a distance that terminates before the outer surface of plurality of first ridges, and wherein the plurality of second ridges are spaced apart along the first central core. The intermediate region transitions between the central core and the central portion.

In some embodiments, the utility device further comprises a second intermediate region; a second central core; and a second tip portion surrounding the second central core and spaced away from the first tip portion by the central portion. In some embodiments, the second tip portion comprises: a second end; a base; a plurality of first ridges extending radially outward from the second central core and extending from the second end of the second tip portion to the base of the second tip portion; and a plurality of second ridges extending between each of the plurality of first ridges, wherein the plurality of second ridges are spaced apart along the first central core.

In some embodiments, the central portion includes a recess. In some embodiments, the central portion includes at least one rib configured to allow a user to grip the central portion. In some embodiments, the plurality of first ridges and the plurality of second ridges intersect to form a plurality of scoops, wherein the scoops are configured to capture material when the first tip portion is applied to a surface. In some embodiments, the first tip portion is integrally formed with the intermediate region. In some embodiments, the top wall and the bottom wall of the plurality of second ridges are substantially flat. In some embodiments, a second ridge of the plurality of second ridges is substantially parallel to an adjacent second ridge of the plurality of second ridges.

In some embodiments, the plurality of secondary ridges includes a first secondary ridge, a second secondary ridge, a third secondary ridge, and a fourth secondary ridge. In some embodiments, adjacent secondary ridges of the plurality of ridges are spaced apart along the first central core by at least 0.070 inches. In some embodiments, the first secondary ridge is positioned adjacent the base and the second secondary ridge, wherein the second secondary ridge is positioned adjacent the first secondary ridge and the third secondary ridge, wherein the third secondary ridge is positioned adjacent the second secondary ridge and the fourth secondary ridge, and wherein the fourth secondary ridge is positioned adjacent the third secondary ridge and the first end. In some embodiments, the first secondary ridge is spaced apart from the second secondary ridge by approximately 0.079 inches. In some embodiments, the second secondary ridge is spaced apart from the third secondary ridge by approximately 0.075 inches. In some embodiments, the third secondary ridge is spaced apart from the fourth secondary ridge by approximately 0.070 inches.

According to some embodiments, a utility device is configured for insertion into an ear. The utility device comprises: a first central core; a first tip portion surrounding the first central core; an intermediate region; and a central portion comprising at least three ribs that extend circumferentially about the central portion, wherein the at least three ribs are configured to allow a user to hold the utility device, and wherein the intermediate region transitions between the central core and the central portion. The first tip portion includes a first end; a base; a plurality of first ridges extending radially outward from the first central core and extending from the first end of the first tip portion to the base of the first tip portion, wherein the plurality of first ridges include a first sidewall and a second sidewall connected by an outer surface; and a plurality of second ridges, wherein the plurality of second ridges include a top wall and a bottom wall, wherein the top wall and the bottom wall form a second ridge edge at the intersection between the top wall and the bottom wall, wherein the second ridge edge contact the first side wall of a first ridge of the plurality of first ridges and the second sidewall of an adjacent first ridge of the plurality of first ridges.

In some embodiments, the plurality of first ridges are configured to extend radially outward from the first central core a first maximum distance and the plurality of second ridges are configured to extend radially outward from the first central core a second maximum distance, wherein the first maximum distance is greater than the second maximum distance.

In some embodiments, the intermediate portion includes a frusto conical portion configured to connect the first central core with the central portion. In some embodiments, the first tip portion includes at least four sets of scoops formed by the intersection of the plurality of first ridges and the plurality of second ridges.

According to some embodiments, a utility device is configured for insertion into an ear. The utility device comprises: a first tip portion; an intermediate region; and a central portion configured to allow a user to hold the utility device, wherein the intermediate region connects the first tip portion and the central portion. The first tip portion includes: a first end; a base; a first ridge; a second ridge comprising: a top wall; and a bottom wall spaced apart from the top wall by an outer surface, wherein the first ridge extends between the second ridge and an adjacent second ridge, wherein the first ridge is configured to support the second ridge and the adjacent second ridge; wherein the first ridge and an adjacent first ridge are connected by an inner concave wall.

In some embodiments, the second ridge and the adjacent second ridge are disc-shaped. In some embodiments, the top wall and the bottom wall of the second ridge are substantially flat. In some embodiments, the first ridge is perpendicular to the top wall and the bottom wall of the second ridge. In some embodiments, the inner concave wall, at least one first ridge and the top and bottom walls of the second ridge form a scoop configured to capture material when the first tip portion is applied to a surface. In some embodiments, the central portion includes at least one rib configured to allow a user to grip the central portion. In some embodiments, the central portion includes a recess.

BRIEF DESCRIPTION OF THE DRAWINGS

The following drawings and the associated descriptions are provided to illustrate embodiments of the present disclosure and do not limit the scope of the claims.

DETAILED DESCRIPTION

Figure 1:
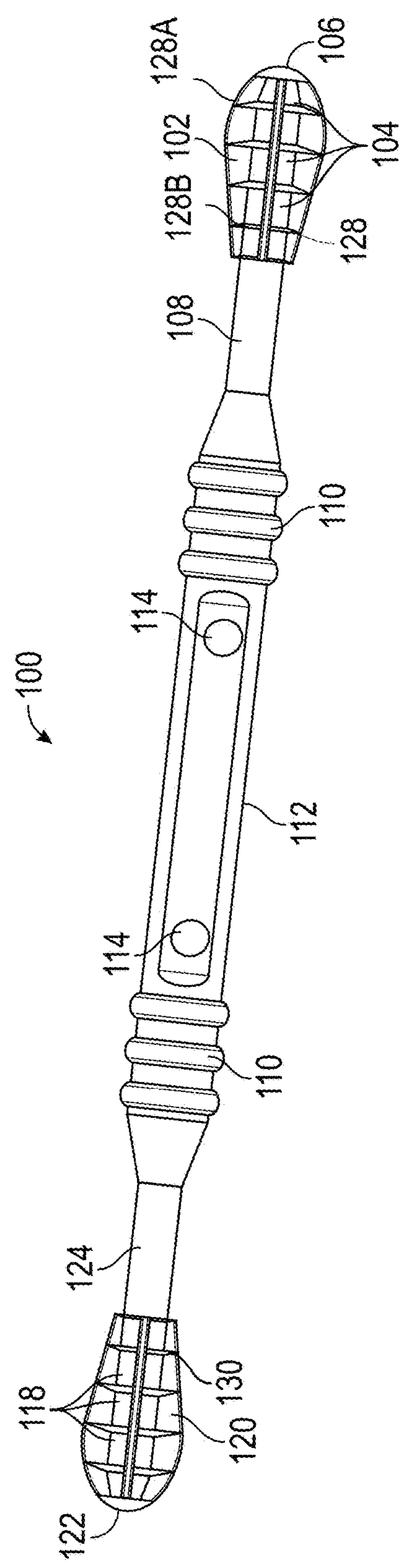
FIG. 1 illustrates an embodiment of a utility device.

To facilitate a complete understanding of the disclosure, the remainder of the detailed description describes the disclosure with reference to the drawings, wherein like reference numbers are referenced with like numerals throughout.

The device may comprise one, two, or more tip portions. The one, two, or more tip portions may be substantially cylindrical, spherical, ellipsoidal, among other shapes. Each of the one, two, or more tip portions may be configured to slide over an intermediate portion. In some embodiments, each of the one, two, or more tip portions is integrally formed with the intermediate portion such that the intermediate portion and at least a portion of the tip portion forms a unitary body.

Each of the one or more tip portions may comprise a plurality of ridges. Generally, each of the plurality of ridges may extend radially outwardly from the tip portion. The plurality of ridges are described in more detail below.

There are many advantages to using the utility device described therein. The utility device may advantageously be more versatile than a traditional cotton swab. Some embodiments of the utility device may be reusable and/or can be cleaned. In some embodiments, the utility device is flexible and/or rigid to enhance the usability. The utility device may advantageously be used more efficiently than traditional cleaning devices. For example, the utility device may comprise a tip portion comprising scoops (for example as formed by ridges) and/or ridges. When the user is using the utility device, the scoops and/or ridges may advantageously allow a user to apply and/or insert the utility device to an ear and/or an outer surface of an ear, a crevice, and/or any other surface only once to effectively clean the targeted ear, crevice, gap, and/or other surface. In other embodiments, the utility device may be applied more than once. In an embodiment, the user may apply the utility device by using a twisting and/or pulling method. In particular, in an embodiment of the utility device used to clean and/or remove earwax or other substance, the scoops and/or ridges would allow the user to remove earwax using a twisting and pulling method. This would, for example, eliminate repetitive ear penetrations when cleaning the ear. In some embodiments, the utility device 100 can be applied to a surface by swiping, brushing, and/or dabbing at least one of the first tip portion 102 and/or the second tip portion 122 along the surface.

The utility device may be made of plastic, rubber, metal, cotton, and/or other materials. For example, the material of the utility device 100 can desirably provide flexibility and/or dexterity to the device. In particular, the utility device 100 can include polyethylene, such as high density polyethylene ("HDPE"), medium density polyethylene ("MDPE"), and/or low density polyethylene ("LDPE"). In some embodiments, the density can be defined by a range of approximately 0.910 to 0.940 g/cm$^3$, 0.926 to 0.940 g/cm$^3$, 0.890 to 0.940 g/cm$^3$, 0.900 to 0.920 g/cm$^3$, 0.900 to 0.910 g/cm$^3$, 0.910 to 0.930 g/cm$^3$, 0.930 to 0.940 g/cm$^3$, and/or 0.940 to 0.950 g/cm$^3$, 0.930 to 0.970 g/cm$^3$, and/or 0.950 to 0.970 g/cm$^3$, among other ranges. The density of the material implemented in the utility device 100 can advantageously increase the flexibility, resiliency, dexterity and/or softness of the device. Similarly, the material of the utility device 100 can minimize or reduce cracking in the utility device 100 when the device is bent and/or otherwise flexed. Use of the invention disclosed herein is not limited to cleaning an ear and removing earwax. The utility device can be used in crafts, electronics, mechanics, personal care, first aid, pet care and/or the like.

In some embodiments, the utility device 100 can include a coating. The coating can be applied through various application arrangements. For example, the coating can be applied by spraying, dipping, pressure treating, and/or directly applying (e.g., brushing) the coating to the utility device 100. In some embodiments, the coating includes various materials, such as rubber, plastic, paint, and/or adhesives, among other chemicals or materials. The coating can be applied during and/or after manufacturing of the utility device 100. The coating can desirably increase the durability of the utility device 100. In some embodiments, the coating enhances the effect of the utility device 100 in use. For example, the coating can allow the utility device 100 to more thoroughly clean the targeted surface.

In some embodiments, the coating can indicate a custom color and/or design. For example, the coating can include a color and/or a plurality of colors. The colors can desirably allow the user to differentiate between one or more utility devices. In some embodiments, the color can be applied to the entire utility device 100. In some embodiments, the color can be applied to only a portion of the utility device 100. For example, the color can be applied to at least a first tip portion 102, a second tip portion 122, one or more ribs 110, a central portion 112, and/or an intermediate portion 108 (described in more detail below), among other portions. In some embodiments, the color may be formed with the material of the utility device 100.

FIG. 1 illustrates an embodiment of utility device 100 comprising a first tip portion 102 and a second tip portion 122. Some embodiments may comprise one tip portion. In some embodiments, the utility device 100 comprises a handle. For example, the handle can connect the first tip portion 102 and the second tip portion 122. In some embodiments, the handle can be connected to and/or formed with the first tip portion 102 and can have a free end that is not connected to and/or formed with the second tip portion 102.

The first tip portion 102 may comprise a first edge 106. The first edge 106 can be flat, rounded, hollowed, and/or the like. In some embodiments, the first edge 106 is integrally formed with the first tip portion 102. In some embodiments, the edge 106 forms a cap that encloses at least a portion of the first tip portion 102. For example, the first edge 106 can be configured to provide a smooth end to advantageously increase comfort to the user during use and/or decrease the risk that the utility device 100 will cause damage to the surface of application area.

The first tip portion 102 comprises a plurality of ridges 128. In some embodiments, the first tip portion 102 includes one, two, three, four or more ridges 128. The plurality of ridges 128 can extend from an inner core of the first tip portion 102. As shown in at least FIG. 1-6, the plurality of ridges 128 can include a plurality of first ridges 128A and a plurality of second ridges 128B. The plurality of first ridges 128A can extend radially outward from the core of the first tip portion 102 and can extend in at least a first direction. For example, the plurality of first ridges 128A can extend along and/or substantially parallel to a longitudinal axis of the utility device 100. The plurality of second ridges 128B can extend radially outward from the core of the first tip portion 102 and can extend in at least a second direction different from the first direction. For example, the plurality of second ridges 128B can extend along and/or substantially parallel to a transverse axis of the utility device 100.

In some embodiments, the plurality of first ridges 128A can extend radially outward for a first distance and the plurality of second ridges 128B can extend radially outward for a second distance. In some embodiments, the first distance is greater than the second distance at the intersection of at least one of the plurality of first ridges 128A and at least one of the plurality of second ridges 128B and/or at the point of connection between at least one of the plurality of first ridges 128A with at least one of the plurality of second ridges 128B. For example, in some embodiments, the plurality of second ridges 128B does not extend beyond an outer edge of the plurality of first ridges 128A. In some embodiments, the plurality of second ridges 128B extends radially outward from the core and/or center of the first tip portion 102 for the second distance and does not reach the edge of the corresponding plurality of first ridges 128A. For example, the plurality of second ridges 128B can have an edge that does not intersect with an edge of the plurality of first ridges 128A. Instead, the edge of the plurality of second ridges 128B may intersect with a first and/or second side wall of the plurality of first ridges 128A. In such configurations, the edge of the plurality of second ridges 128B may terminate before the edge of the plurality of first ridges 128A (e.g., the plurality of first ridges 128A extend radially outward from the central core of the first tip portion a distance greater than the plurality of second ridges 128B) (see, e.g., FIG. 8). In some embodiments, the second distance of 128B can be limited so that it does not break a plane created between the outer edges of any two consecutive first ridges 128A. This has the effect preventing or lessoning the second ridges contact with the application surface.

In some embodiments, such configurations can increase effectiveness of the utility device 100. For example, when a user typically inserts a cotton swab and/or other cleaning device into a user's ear, since the outer shape of the swab or device is generally uniform, earwax and/or other materials described herein may be pushed further into the ear or away from the device. However, according to certain embodiments described herein, the plurality of first ridges 128A may contact an inner surface of the user's ear and/or the target surface. In such configurations, the plurality of first ridges 128A can push the user's skin apart. For example, at least the edges of the plurality of ridges 128A can contact the user's skin and create space for the insertion of the utility device 100 into the ear while minimizing compacting earwax or other debris. The plurality of second ridges 128B are designed to not directly contact an inner surface of the user's ear and/or the target surface. Accordingly, after insertion of the utility device 100 into an ear and twisting the utility device 100, earwax, among other materials are pushed or scraped from the inner ear surface and directed into the scoops created by the first and second ridges 128A and 128B. The second ridges 128B then hold the removed debris when the device is removed from the ear. As such, the plurality of second ridges 128B may be prevented from contacting the target surface (e.g., the inner surface of the user's ear) during insertion or initial contact, but instead may effectively capture and retain the earwax or other material within the scoops until the user pulls back the utility device 100 from the cleaning site. The utility device 100 can thus capture and retain earwax within the scoops of the first tip portion 102 using the twisting and/or pulling method. For example, in some embodiments, the scoops 104 can advantageously allow a user to insert and/or apply utility device

100 to a target surface (e.g. the inner surface of an ear) only once using the twisting and/or pulling method.

In some configurations, a second ridge of the plurality of second ridges 128B can intersect and/or connect to an inner surface of a sidewall of a first ridge of the plurality of first ridges 128A. In some embodiments, the second ridge does not extend outwardly from the core of the first tip portion 102 beyond a maximum first distance of the first ridge. In some embodiments, the second ridge extends outwardly from the core of the first tip portion 102 a greater distance than a portion of the first ridge and a lesser distance than another portion of the first ridge (for example, see FIG. 9). In some embodiments, the second ridge does not extend continuously about the first tip portion 102. For example, the second ridge may extend from an inner surface of a first ridge to an inner surface of another first ridge. In some embodiments, the first ridge does not extend continuously about the first tip portion 102. For example, the first ridge may extend from an inner surface of a second ridge to an inner surface of another second ridge.

As discussed above, the plurality of second ridges 128B can intersect with an outer edge of the plurality of first ridges 128A and/or a side wall of the plurality of first ridges 128A such that the walls of the plurality of first ridges 128A and the walls of the plurality of second ridges 128B form at least one scoop 104. Each of the first tip portion 102 and/or the second tip portion 122 can comprise a plurality of scoops 104. Each of the plurality of scoops 104 may be uniformly shaped. In some embodiments, the shape of each of the plurality of scoops 104 is non-uniform. As described above, the scoops 104 advantageously allow a user to insert and/or apply utility device 100 only once using a twisting and/or pulling method.

In some embodiments, the plurality of ridges can be soft or tough. For example, at least some of the plurality of ridges can be flexible and/or bendable when applied to a surface and at least some of the plurality of ridges can be stiff and/or tough when applied to a surface. In some embodiments, the plurality of ridges are thin to enhance flexibility. For example, in some embodiments, the plurality of first ridges and/or the plurality of second ridges can have an outer edge formed at the intersection of top and bottom walls and/or first and second side walls of each of the plurality of first ridges and the plurality of second ridges. For example, in some configurations, the plurality of second ridges forms a generally triangular shape such that the top and bottom walls of the plurality of second ridges 228B form an edge. Such configurations can advantageously enhance flexibility and allow the plurality of first ridges and/or the plurality of second ridges to bend and/or flex when applied to a surface. In some embodiments, the plurality of ridges may be stronger at the base of the ridge than at the edge of the ridge, increasing flexibility. In some embodiments, the plurality of first ridges and/or the plurality of second ridges has an outer surface that connects the top and bottom walls and/or the first and second side walls of each of the plurality of first ridges and the plurality of second ridges.

In some embodiments, the plurality of ridges may be of the same or varying diameters and sizes. For example, as shown in FIGS. 1-6, the plurality of ridges can be generally convex along an edge of the plurality of ridges. In some embodiments, the plurality of ridges can be generally concave along an edge of the plurality of ridges. In some embodiments, the plurality of ridges can extend outwardly and/or can be flared from a center of the tip portion 102 and/or the core of the tip portion 102 at an angle. In some embodiments, the angle is 90 degrees. In some embodiments, the angle is greater and/or less than 90 degrees.

Generally, utility device 100 may comprise one, two, or more intermediate portions. Each of the one, two, or more intermediate portions may be cylindrical and/or any other shape. Each of the one, two, or more intermediate portions can be hollow and/or solid. As described above, first intermediate portion 108 can be integrally formed with the first tip portion 102 to form a unitary body. In some embodiments, first intermediate portion 108 may be flat at a proximal end near the first tip portion 102. In some embodiments, first intermediate portion 108 is tapered at the proximal end. Intermediate portion 108 may abut first edge 106 and/or abut or couple to an edge of the first tip portion 102.

The Intermediate portion 108 may be integrally formed with a central portion 112. In some embodiments, the central portion 112 is a handle. The intermediate portion 108 may comprise a first length. The intermediate portion 108 may smoothly transition into the central portion 112 and/or with an edge with the central portion 112. The transition from the intermediate portion 108 may comprise a flat surface. The smooth transition from the intermediate portion 108 to the central portion 112 may comprise a tapered surface such that the central portion 112 has a diameter larger than the intermediate portion 108.

In some embodiments, the central portion 112 can have a diameter equal to or smaller than the diameter of intermediate portion 108 in some embodiments.

The central portion 112 can comprise one or more ribs 110. The Ribs 110 may be centrally located along at least a portion of central portion 112. In the illustrated embodiment, the ribs 110 are offset from a central transverse axis. The ribs 110 may be rounded and/or squared. In some embodiments, the central portion 112 comprises one, two, three, four, five, six, seven, eight, nine, and/or ten or more ribs. The central portion 112 can comprise one or more sets of ribs 110. In some embodiments, the ribs 110 may extend radially and outwardly from central portion 112. For example, the ribs 110 may extend about an entire perimeter of the central portion 112 and/or only a portion of the perimeter of the central portion 112.

Figure 2:
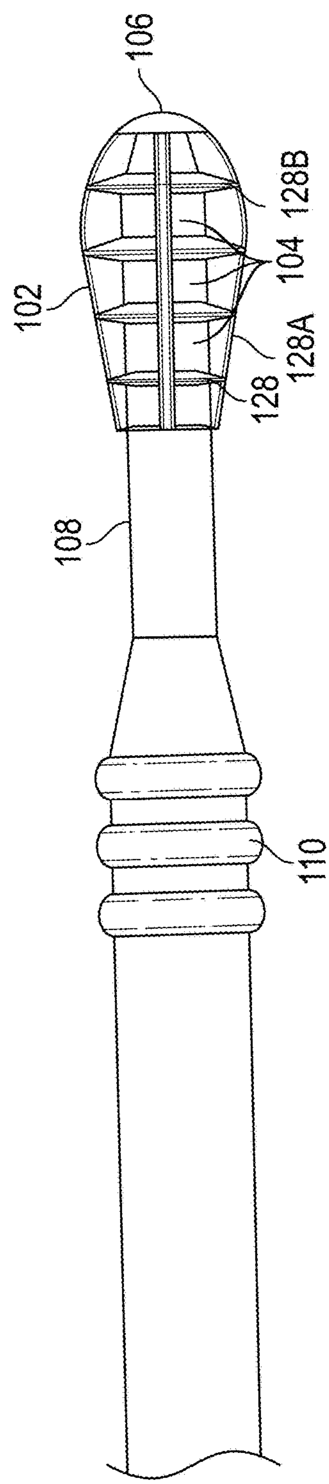
FIG. 2 illustrates an embodiment of a utility device.

In some embodiments, the central portion 112 can be hollow. In some embodiments, the central portion 112 can be solid. As illustrated in FIGS. 1-2, the central portion 112 can comprise one, two, or more holes 114. The holes 114 may extend partially into or through central portion 112. In some embodiments, holes 114 may be injection ports.

Figure 3A:
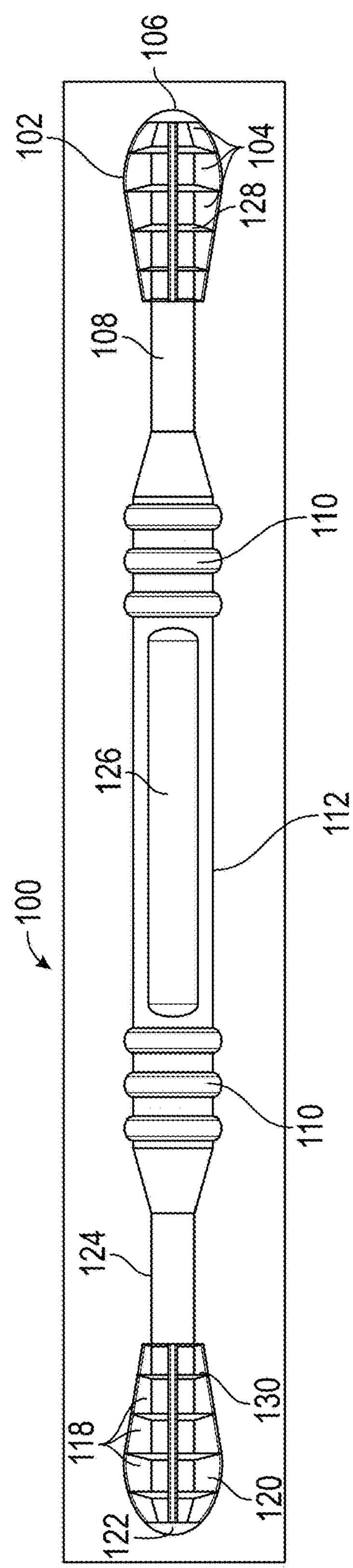
FIG. 3A illustrates a top view of an embodiment of a utility device.
Figure 3B:
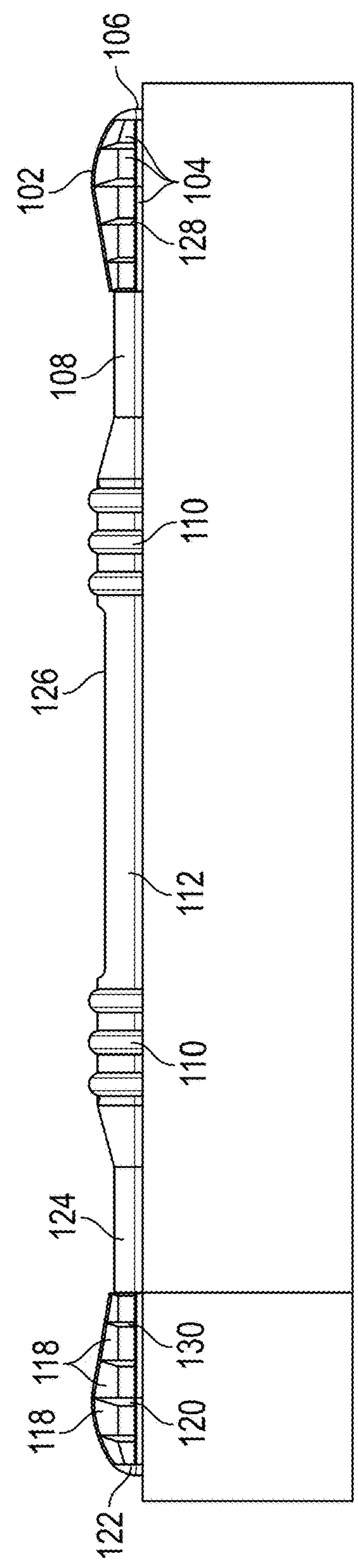
FIG. 3B illustrates a side view of an embodiment of a utility device.
Figure 4:
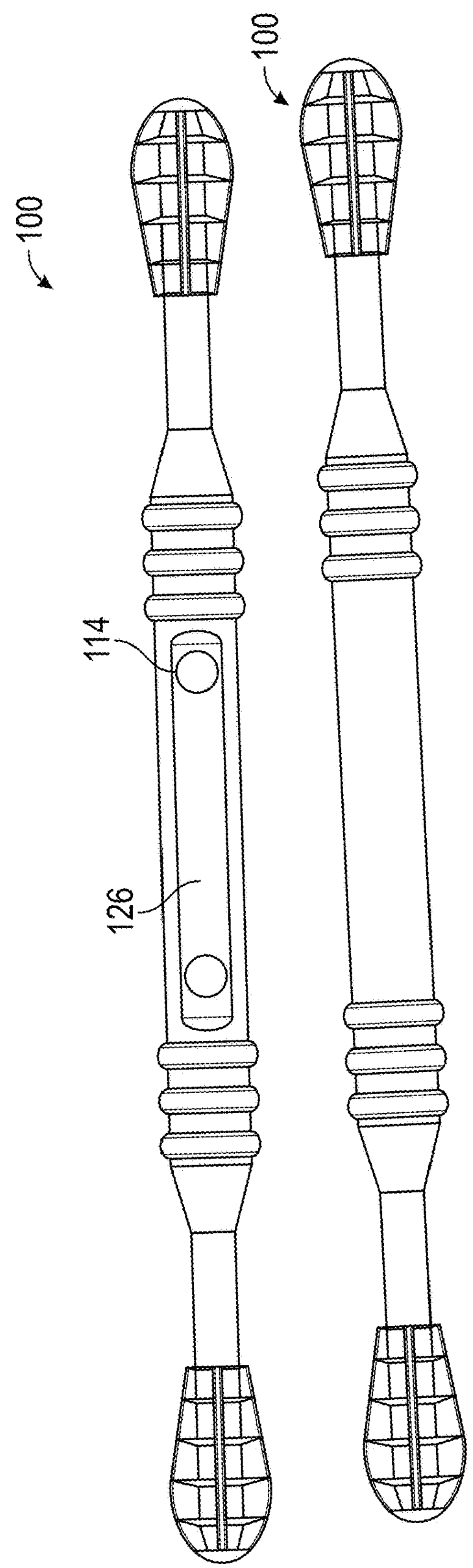
FIG. 4 illustrates an embodiment of a utility device.

FIGS. 3-4 illustrate embodiments of the utility device 100. The utility device 100 can comprise a central portion 112 having a recess 126. Recess 126 can be substantially rectangular, oval, circular, and/or any other shape. The recess 126 can be flat and/or rounded. The recess 126 may advantageously provide the user with additional support and/or a grip for holding utility device 100.

FIG. 4 illustrates an embodiment of utility device 100 comprising recess 126 and one, two, or more holes 114.

In some embodiments, the utility device 100 comprises a second intermediate portion 124 and a second tip portion 120. The second intermediate portion 124 can have a second length. The second length of the second intermediate portion 124 can be the same as, smaller than, or larger than the first length of the first intermediate portion 108. The second intermediate portion 124 may otherwise be substantially similar to the intermediate portion 108.

In some embodiments, the second tip portion 120 may have a size the same as, larger than, or smaller than a size of the first tip portion 102. The second tip portion 120 may comprise a second edge 122. In some embodiments, the second edge 122 can be flat, rounded, hollowed, and/or the like. Additionally, the second tip portion 122 can comprise a plurality of ridges 130. The plurality of ridges 130 can be the same or otherwise substantially similar to the plurality of rubs 110. For example, each of the plurality of ridges 130 may be the same size or have varying sizes. Each of the plurality of ridges 130 intersect to form a plurality of scoops 118. Each of the plurality of scoops 118 may have a size the same as, larger than, or smaller than a size of each of the plurality of scoops 104. The scoops 118 may be the same and/or otherwise substantially similar to the plurality of scoops 104.

Figure 5:
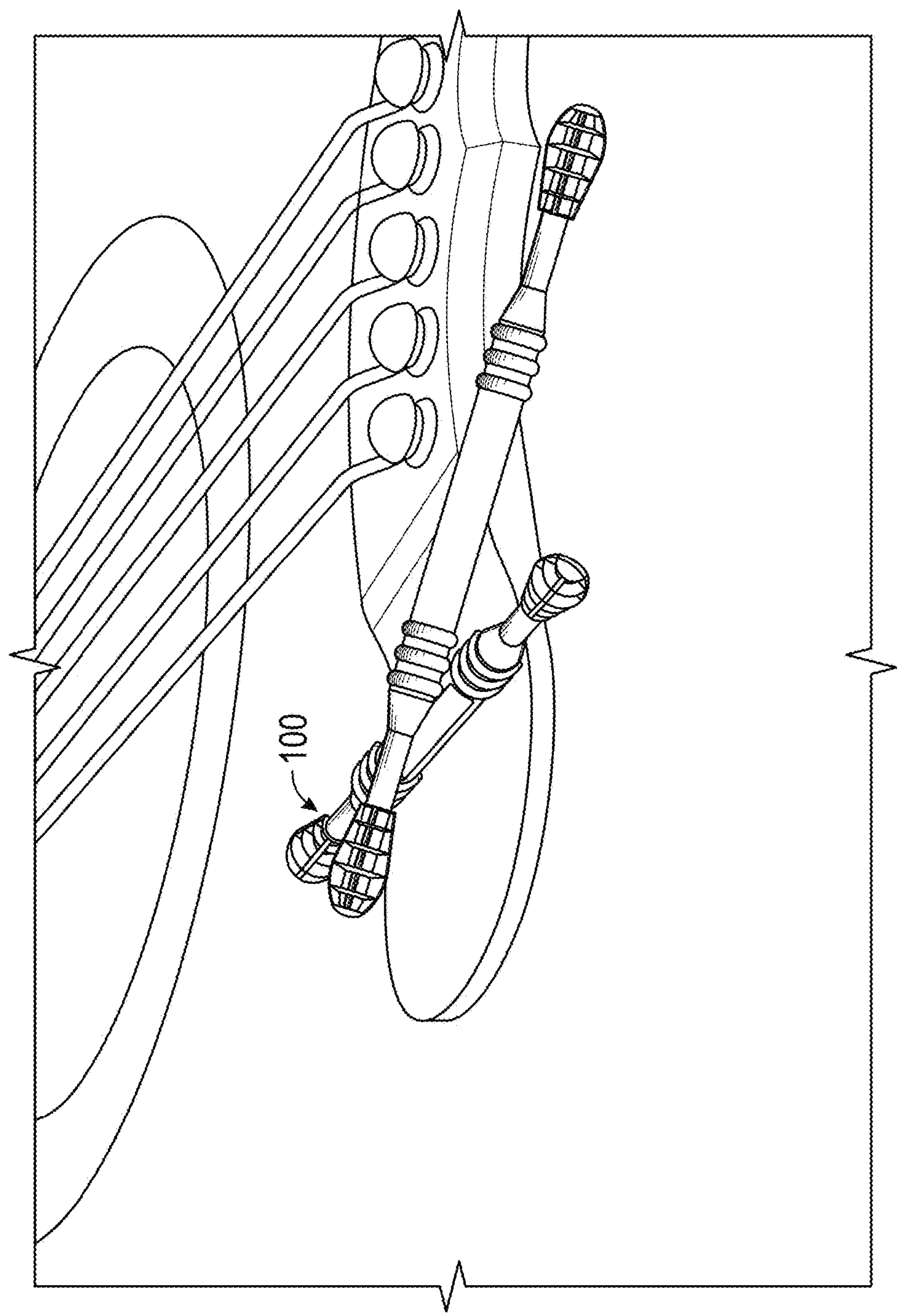
FIG. 5 illustrates a perspective view of an embodiment of a utility device.
Figure 6:
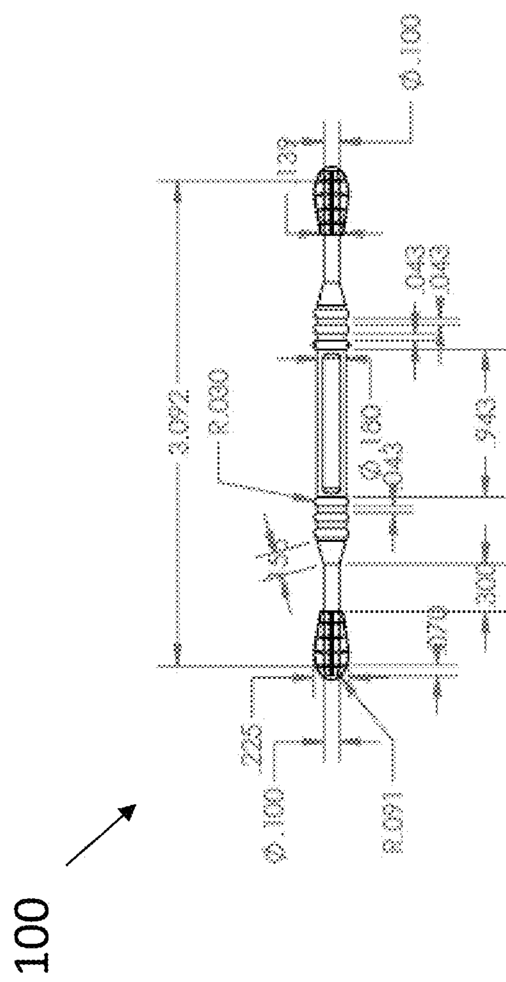
FIG. 6 illustrates a top view of an embodiment of a utility device.

FIGS. 4-6 illustrate various embodiments of utility device 100.

In some embodiments, at least a portion of the utility device 100 can include a marking and/or indicator. For example, the central portion 112 can include an indicator. The indicator can include a label, for example to indicate a color, a brand, and/or other marking. The indicator can desirably be customizable in some configurations. The indicator can be adhered to the utility device 100 by an adhesive, for example. In some embodiments, the indicator can be removably attached to the utility device 100, such as a sticker. However, in some embodiments, the indicator is permanently attached and/or formed with the device. For example, the indicator can be etched into and/or integrated with the utility device 100. In some embodiments, the indicator can be configured to be positioned within the recess.

In some embodiments, the utility device 100 includes a sterilization mechanism. The sterilization mechanism can include a material and/or a device that can sterilize the utility device 100. Accordingly, the utility device 100 may be self-sterilizing. In some embodiments, a sterilizer can be applied to the utility device 100 for sterilizing the utility device 100. Thus, in some embodiments, the utility device 100 is reusable and/or can be cleaned between uses.

FIG. 6 illustrates a top view of an embodiment of the utility device 100. As described above, the utility device 100 can be integrally formed and/or formed by separate components connected and/or otherwise attached. In some embodiments, the utility device can include one or more tip portions. In some embodiments, the utility device 100 can form various shapes and sizes. For example, a length 170 extending from the first tip portion 102 to the second tip portion 122 can be approximately 3.092 inches. In some embodiments, the length 170 is approximately 1 inch, 2 inches, 3 inches, and/or 4 or more inches. In some embodiments, a length 171 of the recess can be approximately 0.943 inches, 0.8 inches, 0.9 inches, and/or 1 or more inches. As discussed above, the central portion can include one or more ribs 110. The ribs 110 can have a width of approximately 0.043 inches. In some embodiments, the width of the ribs is approximately 0.03 inches, 0.04 inches, or 0.05 or more inches. In some embodiments, each rib 110 of the one or more ribs 110 can have varying sizes and shapes. In some embodiments, the rib 110 can be spaced apart from an adjacent rib 110 by 0.043 inches. In some embodiments, the spacing between one rib and an adjacent rib 110 is uniform and/or non-uniform. For example, a rib 110 can be spaced apart from an adjacent rib 110 by 0.02 inches, 0.03 inches, 0.04 inches, or 0.05 inches or more. In some embodiments, the rib 110 can have a radius of approximately 0.03 inches. In some embodiments, the rib 110 can have a radius of more or less than approximately 0.03 inches. In some embodiments, the rib 110 extends outwardly from an outer surface of the central portion 112 by approximately 0.03 inches. In some embodiments, the diameter of the central portion 112 is approximately 0.180 inches, 0.150 inches, 0.200 inches, or more.

In some embodiments, the intermediate portion 108 includes a straight portion 108A and a frusto conical portion 108B. In some embodiments, the outer taper of the frusto conical portion 108B is approximately 0.150 inches, 0.1 inches, or 0.2 inches or more. In some embodiments, the straight portion 108A has a length of approximately 0.3 inches, 0.1 inches, 0.2 inches, 0.3 inches, or 0.4 inches or more.

In some embodiments, a diameter of the intermediate portion and/or the core of the tip portion 102 is approximately 0.091 inches or 0.100 inches. In some embodiments, the diameter of the intermediate portion and/or the core of the tip portion 102 is greater than or less than 0.100 inches.

In some embodiments, the tip portion 102 extends outwardly from the core. In some embodiments, the tip portion 102 extends outwardly from the core various lengths along the tip portion 102. For example, the base of the tip portion 102 can have a diameter of approximately 0.139 inches, 0.130 inches, 0.140 inches, or 0.150 inches or more. In some embodiments, the edge of the tip portion 102 has a diameter of approximately 0.100 inches. In some embodiments, the tip portion 102 extends outwardly at a maximum point 173. In some embodiments the diameter of the tip portion 102 at the maximum point is approximately 0.225 inches. In some embodiments, the diameter of the tip portion 102 at the maximum point is greater than or less than 0.225 inches. In some embodiments, the distance between the maximum point of the first tip portion 102 to the maximum point of the second tip portion 122 is approximately 3.092 inches. In some embodiments, a distance 174 from the maximum point to the first edge 106 is approximately 0.070 inches. In some embodiments, the distance 174 is less than a longitudinal distance between the maximum point and the base of the first tip portion 102. In some embodiments, the distance 174 is greater than a longitudinal distance between the maximum point and the base of the first tip portion 102

Figure 7:
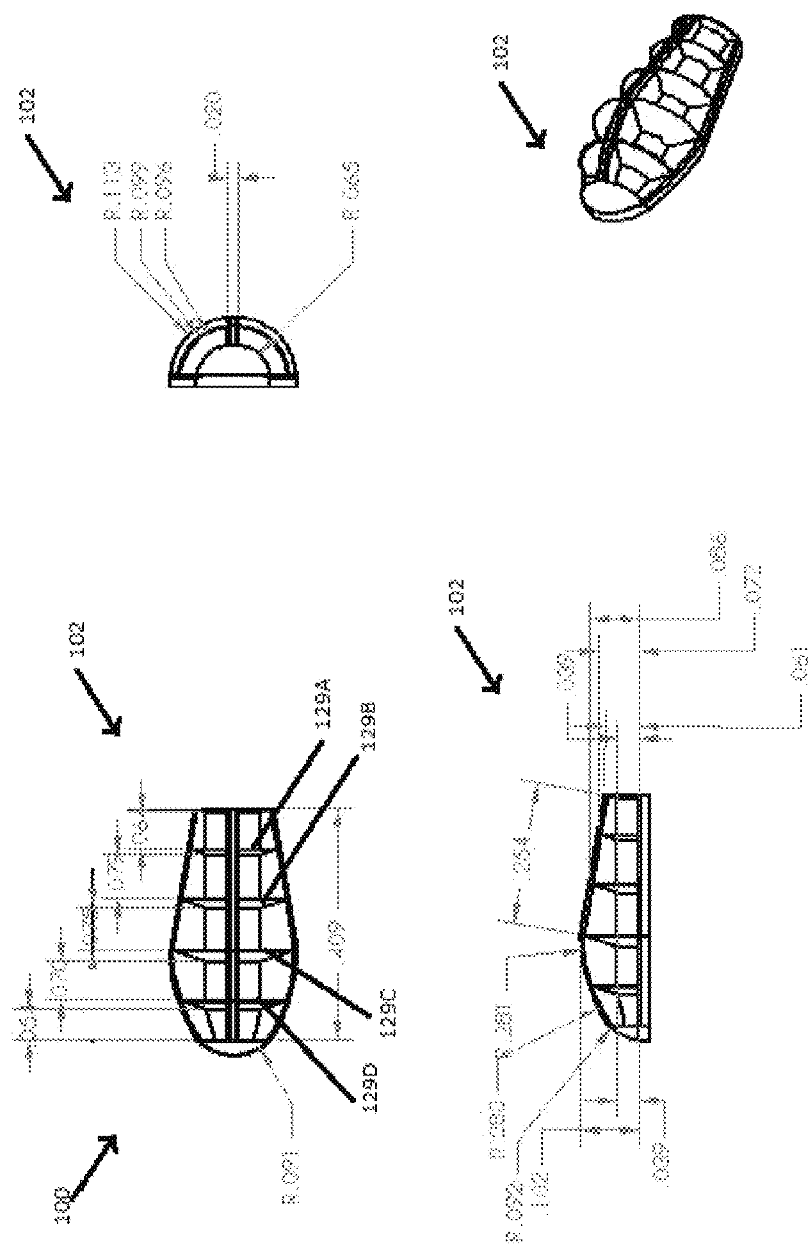
FIG. 7 illustrates a tip portion of an embodiment of a utility device.

FIG. 7 illustrates an example embodiment of the first tip portion 102 of the utility device 100. In some embodiments, the plurality of second ridges are spaced apart along the longitudinal axis of the utility device 100. In some embodiments, the spacing between adjacent second ridges 128B can enhance effectiveness. For example, the spacing can allow larger pieces or chunks of debris to be removed by the utility device 100 in use. Such configurations may not compact, smear, and/or push the debris within the ear. Rather, when the tip portion 102 is inserted into the ear and debris is removed from the ear, larger chunks of debris can be captured within the scoops of the tip portion 102 and be removed from the ear.

In some embodiments, a minimum amount of spacing between adjacent second ridges 128B can enhance usability and effectiveness. For example, as shown in FIG. 7, the first tip portion can include at least four second ridges 128B. In some embodiments, the first tip portion can include at least one, two, three, five, six, or seven second ridges 128B. As shown in FIG. 7, the second ridge 129A can be spaced apart from the base of the first tip portion 102 by at least 0.964 inches. The second ridge 129A can be spaced apart from the second ridge 129B by at least 0.079 inches. In some embodiments, the second ridge 129B can be spaced apart from a second ridge 129C by at least 0.075 inches. In some embodiments, the second ridge 129C can be spaced apart from a second ridge 129D by at least 0.070 inches. In some embodiments, the second ridge 129D can be spaced apart from the edge 106 by at least 0.054 inches. In some embodiments, adjacent second ridges can be spaced apart from one another by at least 0.070 inches. In some embodiments, adjacent second ridges can be spaced apart from one another by 0.065 inches, 0.0675 inches, 0.070 inches, 0.0725 inches, 0.075 inches, 0.0775 inches, 0.080 inches, and/or 0.0825 or more inches. In some embodiments, the edge 106 is spaced apart from the base of the tip portion by approximately 0.409 inches.

In some embodiments, the second ridges 128B extends outwardly from the central longitudinal axis by varying lengths and have various radii. For example, in some embodiments, the second ridge 129A has a radius of approximately 0.081 inches. In some embodiments, the second ridge 129B has a radius of approximately 0.099 inches. In some embodiments, the second ridge 129B has a radius of approximately 0.096 inches. In some embodiments, the second ridge 129C has a radius of approximately 0.130 inches. In some embodiments, the second ridge 129D has a radius of approximately 0.096 inches. In some embodiments, the cover or end 106 has a radius of approximately 0.065 inches.

As shown in FIG. 7, the plurality of first edges 128A can have varying thicknesses. In some embodiments, the thickness of the plurality of first edges 128A is approximately 0.020 inches. In some embodiments, the thickness of the plurality of first edges 128A is greater than or less than 0.020 inches.

Figure 8:
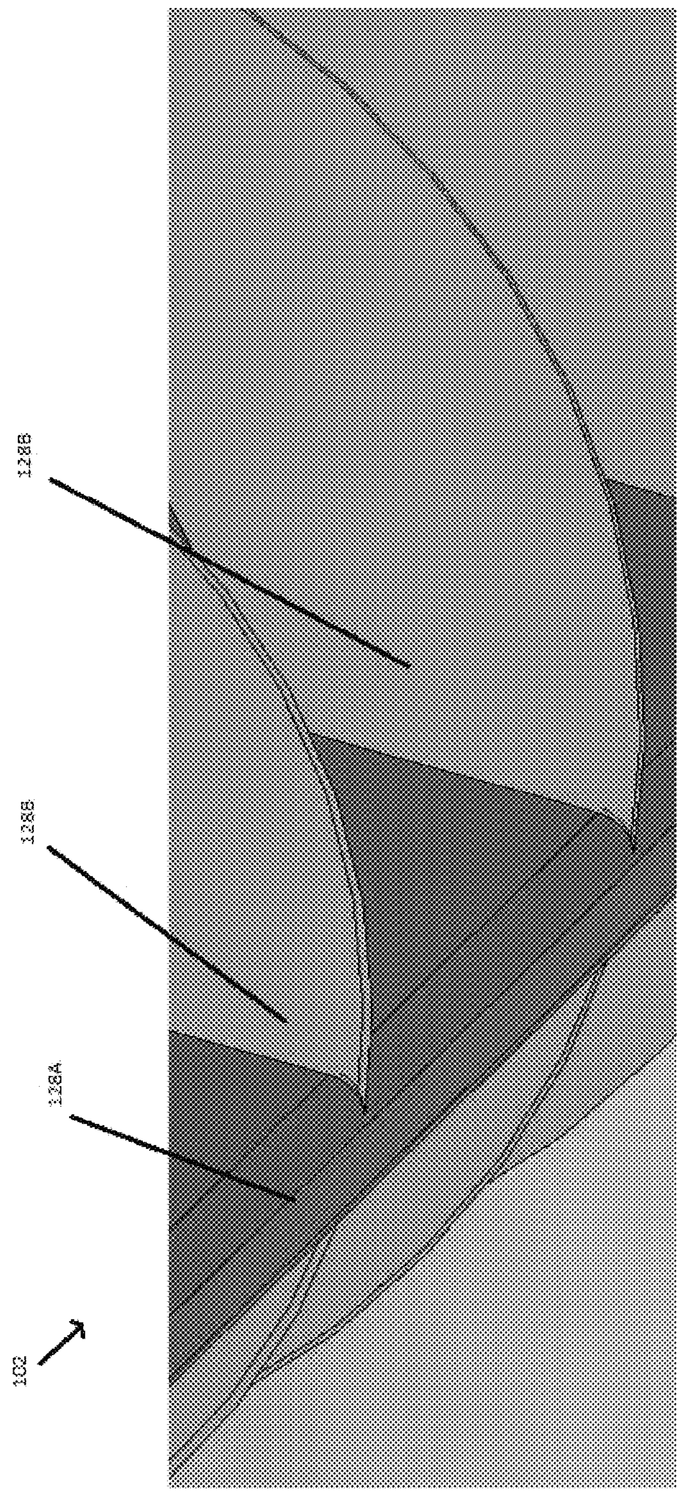
FIG. 8 illustrates a close-up view of a tip portion of an embodiment of a utility device.

FIG. 8 illustrates a close-up view of the first tip portion 102 of an embodiment of the utility device 100. As shown in FIG. 8 and as discussed above, the plurality of second ridges 228B can be recessed relative to the plurality of first ridges 228A. For example, the plurality of first ridges 228A can extend outwardly from a central longitudinal axis of the utility device 100 further than the plurality of second ridges 228B. In such configurations, the outer edge of the plurality of second ridges 228B may intersect with a side wall of the plurality of first ridges 228A rather than the outer surface and/or outer edge of the plurality of first ridges 228A. Such configurations may advantageously limit damage to the inner surface of the ear, as such configurations may limit the number of ridges contacting the inner surface of the ear. For example, in some embodiments, only the plurality of first ridges may contact the inner surface of the ear. In some embodiments, only four first ridges 128A may contact the inner surface of the ear. In some embodiments, one, two, three, five, six, and/or seven ridges may contact the inner surface of the ear.

As discussed above, at least one second ridge 128B may be recessed relative to the plurality of first ridges 128A. Such configurations can help to reduce and/or elimination negative suction. For example, if the outer edge of the plurality of second ridges 128B intersected with the outer edge or surface of the plurality of first ridges 128A, creating a substantially uniform outer surface, a honeycomb structure may be formed that creates a suctioning effect. Thus, when the tip portion is inserted into the ear, the tip portion may cause a suctioning effect in each of the scoops. In such circumstances, the scoops may pull on the inner surface of the ear and cause damage. In certain configurations described herein in which the plurality of second ridges 128B are recessed relative to the plurality of first ridges 128A, a suctioning effect may be reduced since the outer surface of the tip portion 102 may not be uniform. In such configurations, the outer edge of the plurality of second ridges 128B would be spaced apart from the inner surface of the ear, creating breathing room between the tip portion and the ear. Accordingly, such configurations may reduce damage to the ear.

Figure 9:
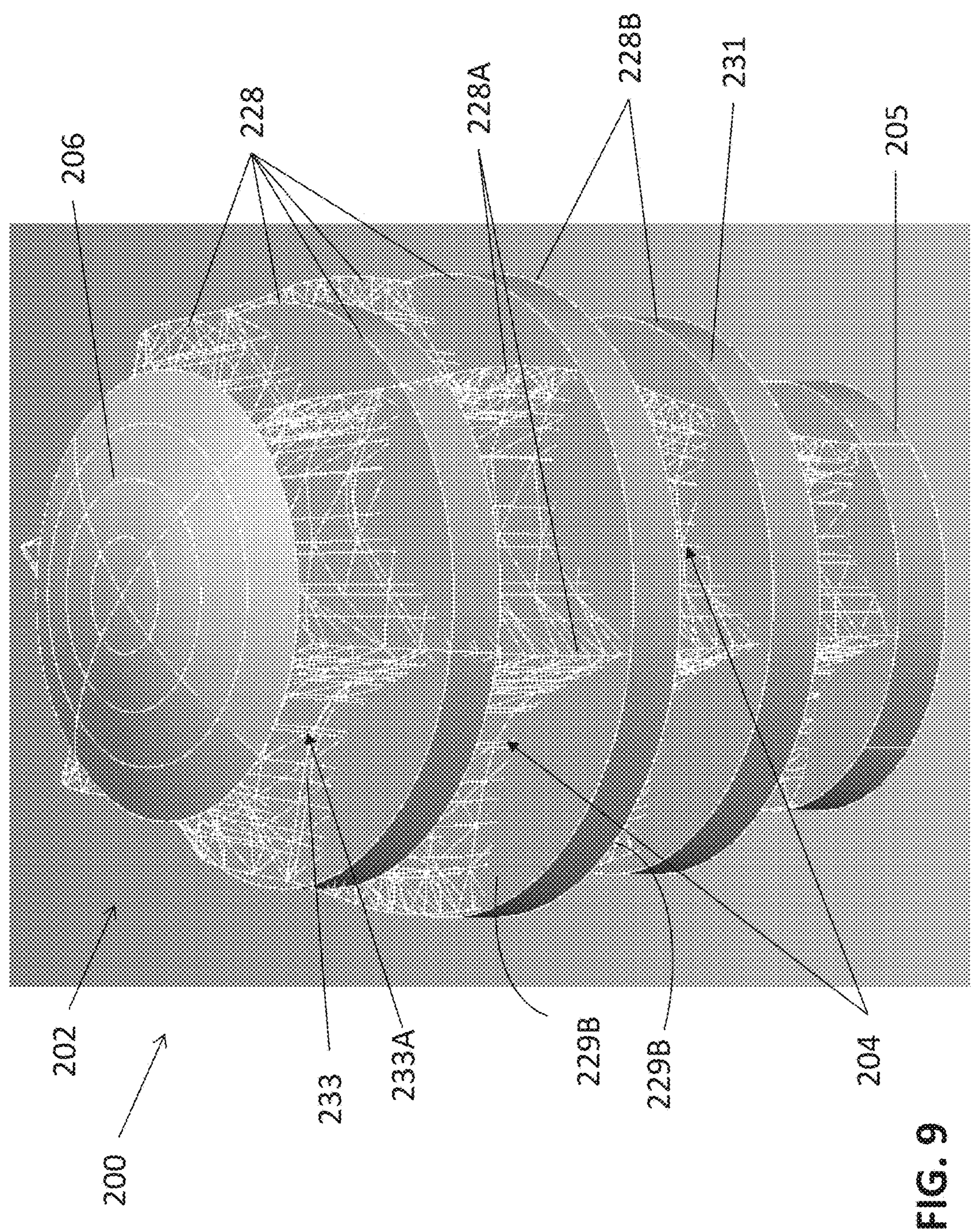
FIG. 9 illustrates a tip portion of an embodiment of a utility device.

FIG. 9 illustrates another embodiment of the utility device 200. The utility device 200 is similar or identical to the utility device discussed above in many respects. As shown in FIG. 9, the utility device 200 can include a first tip portion 202, which can be respectively similar to the first tip portion 102 described above in connection with the utility device 100. The utility device 200 can include any one, or any combination, of features of the utility device 100.

For example, as shown in FIG. 9, the utility device 200 includes a first tip portion 202. The first tip portion 202 can include a plurality of ridges 228. The plurality of ridges 228 may be the same or otherwise substantially similar to the ridges 128 discussed above in connection with the utility device 100.

In some embodiments, the plurality of ridges 228 includes a plurality of first ridges 228A and a plurality of second ridges 228B. As shown in the illustrated embodiment, the plurality of first ridges 228A can extend in a first direction along and/or substantially parallel to the longitudinal axis of the utility device 200 and the plurality of second ridges can extend in a second direction that is along or substantially parallel to a transverse axis of the utility device 200. In some examples, the plurality of second ridges include a disc-like structure. For example, as illustrated in FIG. 9, the plurality of second ridges 228B include top and bottom walls 229A, 229B spaced apart by a flat surface 231. In some configurations, the plurality of second ridges 228B are integrally formed with a core of the first tip portion 202. In some configurations, the first tip portion 202 does not include a core.

In some configurations, the plurality of second ridges 228B are integrally formed and/or connected to the plurality of first ridges 228A. For example, the plurality of first ridges 228A can provide support to the structure of the first tip portion 202. In such configurations, each of the plurality of second ridges 228B can be spaced apart from one another by at least one first ridge 228A. In some embodiments, a first ridge extends from a center of a first edge 206 of the first tip portion 202 to a base 205 of the first tip portion 202. In some embodiments, the first ridge 228A extends from a top wall of a second ridge 228B to a bottom wall of an adjacent second ridge 228B. In some embodiments, a portion of the first ridge 228A extends from the center of the first edge 206 to the base 205 and a portion of the first ridge 228A extends from a top wall 229A of a second ridge 228B to a bottom wall 229B of an adjacent second ridge 228B.

As shown in the illustrated embodiment, a first ridge 228B can be connected to an adjacent first ridge 228B by an inner concave wall 233. For example, as shown in FIG. 9, the inner concave wall 233 has an intermediate region 223A that curves towards the longitudinal axis of the utility device 200. In such configurations, the inner concave wall 233 forms a scoop 204 with the first ridge 228B and the top and bottom walls 229A, 229B of the second ridge 228B.

In some embodiments, the plurality of second ridges 228B provide a shelf to capture earwax, dust, fluid, and/or other materials within the scoops 204 when the first tip portion 202 is applied to a surface, such as an ear. In some embodiments, each of the plurality of scoops 204 of the first tip portion 202 are the same size. In some embodiments, the plurality of scoops 204 positioned near the first edge 206 and/or positioned near the base 205 are smaller than the plurality of scoops 204 positioned near a longitudinal center of the first tip portion 202. In some embodiments, the plurality of scoops 204 positioned near the base 205 are smaller than the plurality of scoops 204 positioned near the first edge 206. As described above in connection with the scoops 104, the scoops 204 can advantageously allow a user to insert and/or apply utility device 200 only once using a twisting and/or pulling method.

Figure 10:
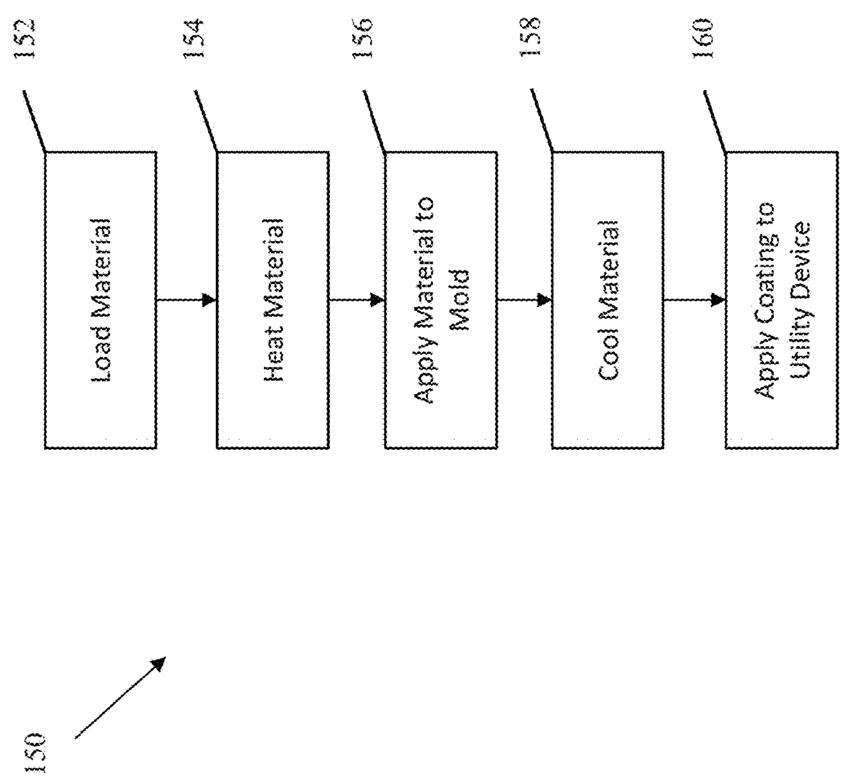
FIG. 10 illustrates an embodiment of a manufacturing process of a utility device.

FIG. 10 illustrates an example method 150 of manufacturing the utility device 100. For example, at block 152, any of the materials describe herein can be loaded into a machine for processing. As shown at block 154, the material can be optionally heated. The material can be heated before and/or after the material is loaded into the machine. Accordingly, the material can be melted or can be soft enough to be injected under pressure to fill a mold, for example. At block 156, the material can be applied to the mold. For example, the mold can be held together while the pressure is applied to the material to inject and/or force the material into the mold. Once the material has filled the mold, the material can be cooled and/or dried at block 158 to desirably harden the material and/or to form the utility device. At block 160, a coating, such as the coating described herein, can be manually and/or automatically applied to the utility device 100.

Other combinations, omissions, substitutions and modifications will be apparent to the skilled artisan in view of the disclosure herein. Accordingly, the present disclosure is not intended to be limited by the reaction of the preferred embodiments. Additionally, all publications, patents, and patent applications mentioned in this specification are herein incorporated by reference to the same extent as if each individual publication, patent, or patent application was specifically and individually indicated to be incorporated by reference.

What is claimed is:

1. A utility device configured for insertion into an ear, the utility device comprising:

a first central core;

a first tip portion surrounding the first central core including:

a first end;

a base;

a plurality of first ridges extending radially outward from the first central core and extending from the first end of the first tip portion to the base of the first tip portion, wherein the plurality of first ridges include a first sidewall and a second sidewall connected by an outer surface;

a plurality of secondary ridges, wherein the plurality of secondary ridges include a top wall and a bottom wall, wherein the top wall and the bottom wall form a secondary ridge edge at the intersection between the top wall and the bottom wall, wherein the secondary ridge edge extends between the first side wall and the second side wall of adjacent first ridges of the plurality of first ridges such that the plurality of secondary ridges extend radially outward from the central core to a distance that terminates before the outer surface of plurality of first ridges, and wherein the plurality of secondary ridges are spaced apart along the first central core;

an intermediate region; and a central portion configured to allow a user to hold the utility device, wherein the intermediate region transitions between the central core and the central portion.

2. The utility device of claim 1, wherein the plurality of secondary ridges includes a first secondary ridge, a second secondary ridge, a third secondary ridge, and a fourth secondary ridge.

3. The utility device of claim 2, wherein the first secondary ridge is positioned adjacent the base and the second secondary ridge, wherein the second secondary ridge is positioned adjacent the first secondary ridge and the third secondary ridge, wherein the third secondary ridge is positioned adjacent the second secondary ridge and the fourth secondary ridge, and wherein the fourth secondary ridge is positioned adjacent the third secondary ridge and the first end.

4. The utility device of claim 3 wherein the first secondary ridge is spaced apart from the second secondary ridge by approximately 0.079 inches.

5. The utility device of claim 3 wherein the second secondary ridge is spaced apart from the third secondary ridge by approximately 0.075 inches.

6. The utility device of claim 3 wherein the third secondary ridge is spaced apart from the fourth secondary ridge by approximately 0.070 inches.

7. The utility device of claim 1, wherein adjacent secondary ridges of the plurality of ridges are spaced apart along the first central core by at least 0.070 inches.

8. The utility device of claim 1, further comprising:

a second intermediate region;

a second central core; and a second tip portion surrounding the second central core and spaced away from the first tip portion by the central portion.

9. The utility device of claim 8, wherein, wherein the second tip portion comprises:

a second end;

a base;

a plurality of first ridges extending radially outward from the second central core and extending from the second end of the second tip portion to the base of the second tip portion; and a plurality of secondary ridges extending between each of the plurality of first ridges, wherein the plurality of secondary ridges are spaced apart along the first central core.

10. The utility device of claim 1, wherein the central portion includes a recess forming a flat surface.

11. The utility device of claim 1, wherein the central portion includes at least one rib configured to allow a user to grip the central portion.

12. The utility device of claim 1, wherein the plurality of first ridges and the plurality of secondary ridges intersect to form a plurality of scoops, wherein the scoops are configured to capture material when the first tip portion is applied to a surface.

13. The utility device of claim 1, wherein the first tip portion is integrally formed with the intermediate region.

14. The utility device of claim 1, wherein the top wall and the bottom wall of the plurality of secondary ridges are substantially flat.

15. The utility device of claim 1, wherein a secondary ridge of the plurality of secondary ridges is substantially parallel to an adjacent secondary ridge of the plurality of secondary ridges.

16. The utility device of claim 1, wherein the secondary ridge edge of the plurality of secondary ridges does not intersect with a plane formed along the outer surface of the plurality of first ridges.

17. A utility device configured for insertion into an ear, the utility device comprising:

a first central core;

a first tip portion surrounding the first central core including:

a first end;

a base;

a plurality of first ridges extending radially outward from the first central core and extending from the first end of the first tip portion to the base of the first tip portion, wherein the plurality of first ridges include a first sidewall and a second sidewall connected by an outer surface; and a plurality of secondary ridges, wherein the plurality of secondary ridges include a top wall and a bottom wall, wherein the top wall and the bottom wall form a secondary ridge edge at the intersection between the top wall and the bottom wall, and wherein the secondary ridge edge contact the first side wall of a first ridge of the plurality of first ridges and the second sidewall of an adjacent first ridge of the plurality of first ridges;

an intermediate region; and a central portion comprising at least one rib that extends circumferentially about the central portion, wherein the at least one rib is configured to allow a user to hold the utility device, wherein the intermediate region transitions between the central core and the central portion; and wherein the plurality of first ridges are configured to extend radially outward from the first central core a first maximum distance and the plurality of secondary ridges are configured to extend radially outward from the first central core a second maximum distance, wherein the first maximum distance is greater than the second maximum distance.

* * * * *